United States Patent [19]

Zeck et al.

[11] Patent Number: 4,690,947
[45] Date of Patent: Sep. 1, 1987

[54] SYNERGISTIC COMPOSITION FOR THE CONTROL OF ARTHROPODS

[75] Inventors: Walter M. Zeck; Donald E. Simonet, both of Vero Beach, Fla.

[73] Assignee: Mobay Corporation, Pittsburgh, Pa.

[21] Appl. No.: 801,454

[22] Filed: Nov. 25, 1985

Related U.S. Application Data

[63] Continuation of Ser. No. 632,137, Jul. 18, 1984, abandoned.

[51] Int. Cl.$^4$ .................... A01N 37/34; A01N 37/52; A01N 57/00; A01N 55/04
[52] U.S. Cl. .................... 514/521; 514/637; 514/128; 514/189; 514/493
[58] Field of Search ........................ 514/521, 637

[56] References Cited

U.S. PATENT DOCUMENTS

| | | | |
|---|---|---|---|
| 4,053,595 | 10/1977 | Zeck et al. | 424/326 |
| 4,087,523 | 5/1978 | Lovell | 424/326 |
| 4,104,376 | 8/1978 | Zeck | 424/326 |
| 4,152,454 | 5/1979 | Plapp, Jr. | 424/326 |
| 4,218,469 | 8/1980 | Fuchs et al. | 424/304 |

FOREIGN PATENT DOCUMENTS 1105833 7/1981 Canada .................... 424/304

OTHER PUBLICATIONS

El-Sayed et al., Journal of Economic Entomology, 77, pp. 23–30 (Feb. 1984).
Rajakulendran et al., Journal of Economic Entomology, pp. 1089–1092 (Dec. 1982).
Plapp, Jr., Journal of Economic Entomology, 69, pp. 91–92, (Aug. 1975).
Plapp, Jr., Journal of Economic Entomology, 72, pp. 667–670, (Oct. 1979).

Primary Examiner—Albert T. Meyers
Assistant Examiner—John M. Kilcoyne
Attorney, Agent, or Firm—Gene Harsh; Lawrence S. Pope

[57] ABSTRACT

Arthropodicidal compositions in the form of synergistic combinations of (A) cyano-(4-fluoro-3-phenoxyphenyl)-methyl 3-(2,2-dichlorovinyl)-2,2-dimethylcyclopropanecarboxylate plus (B) O-ethyl-O-[4-(methylthio)-phenyl]-S-propyl phosphorodithioate, (A) plus (C) $N^1$-(4-chloro-O-tolyl)-N,N-dimethylformamidine, (A) plus (B) plus (C), (A) plus (D) 1-(tricyclohexylstannyl)-1H-1,2,4-triazole, (A) plus (E) tricyclohexyl hydroxystannane, or (A) plus (F) hexakis-(2-methyl-2-phenylpropyl)-distannoxane, which are individually known compounds, which combinations possess synergistic arthropidicidal properties especially for the control of mites.

13 Claims, No Drawings

SYNERGISTIC COMPOSITION FOR THE CONTROL OF ARTHROPODS

This is a continuation of application Ser. No. 632,137, filed July 18, 1984, now abandoned.

The present invention relates to and has for its objects the provision of particular new arthropodicidal compositions in the form of synergistic combinations of (A) cyano-(4-fluoro-3-phenoxyphenyl)-methyl 3-(2,2-dichlorovinyl)-2,2-dimethyl-cyclopropanecarboxylate plus (B) O-ethyl-O-[4-(methylthio)-phenyl]-S-propyl phosphorodithioate, (A) plus (C) $N^1$-(4-chloro-O-tolyl)-N,N-dimethylformamidine, (A) plus (B) plus (C), (A) plus (D) 1-(tricyclohexylstannyl)-1H-1,2,4-triazole, (A) plus (E) tricyclohexyl hydroxystannane, or (A) plus (F) hexakis-(2-methyl-2-phenylpropyl)-distannoxane which are individually known compounds, which combinations possess outstanding synergistic arthropodicidal properties especially for controlling mites optionally in the form of carrier composition mixtures of such synergistic combinations with solid and/or liquid dispersible carrier vehicles, and methods for using such synergistic combinations in a new way especially for combating arthropods, with other and further objects becoming apparent from a study of the within specification and accompanying examples.

U.S. Pat. No. 4,218,469 discloses the insecticide cyano-(4-fluoro-3-phenoxyphenyl)-methyl 3-(2,2-dichlorovinyl)-2,2-dimethyl-cyclopropanecarboxylate.

It is taught in U.S. Pat. No. 3,825,636 that compounds such as O-ethyl-O-[4-(methylthio)-phenyl]-S-propyl phosphorodithioate can be used as insecticides.

U.S. Pat. No. 4,053,595 discloses this active material in a synergistic insecticidal composition with $N^1$-(4-chloro-o-tolyl)-N,N-dimethylformamidine. U.S. Pat. No. 4,104,376 discloses this active material in a synergistic insecticidal composition with N-methyl-$N^1$-2,4-xylyl-N-(N-2,4-xylyl-formimidoyl)-formamidine. Both of these latter compositions are especially effective against insects which attack cotton.

The book "Chemistry of Pesticides" edited by K. H. Buchel, John Wiley & Sons, discloses as acaricides the compounds 1-(tricyclohexylstannyl)-1H-1,2,4-triazole, tricyclohexyl hydroxystannane, and hexakis-(2-methyl-2-phenylpropyl)-distannoxane.

However, there are certain pests, such as mites, which are resistant to these compounds, i.e. either not being killed thereby or requiring large concentrations. Thus, in trying to rid a home or farm of pests including such mites, it becomes necessary to utilize that amount needed for the resistant mites. If lower amounts are used, the other pests will be destroyed but the mites will survive and take over the area.

It is accordingly an object of the invention to provide a composition which is highly active against a large variety of pests, including mites.

It has now been found that combinations of (A) cyano-(4-fluoro-3-phenoxyphenyl)-methyl 3-(2,2-dichlorovinyl)-2,2-dimethyl-cyclopropanecarboxylate plus (B) O-ethyl-O-[4-(methylthio)-phenyl]-S-propyl phosphorodithioate, (A) plus (C) $N^1$-(4-chloro-O-tolyl)-N,N-dimethylformamidine, (A) plus (B) plus (C), (A) plus (D) 1-(tricyclohexylstannyl)-1H-1,2,4-triazole, (A) plus (E) tricyclohexyl hydroxystannane, or (A) plus (F) hexakis-(2-methyl-2-phenylpropyl)-distannoxane are especially effective in fighting arthropods and particularly acarids such as mites, especialy spider mites, although they are also highly effective against many insects.

Advantageously, the weight ratio of A: B+C, D, E or F ranges from about 1:0.1–100, preferably from about 1:0.2–20 and most preferably from about 1:1–10. As noted, either B or C can be absent from B+C, i.e., B+C can be made up of all B or all C.

Surprisingly, the arthropodicidal effectiveness of the particular new synergistic combinations of active compounds according to the present invention is substantially higher than the sum of the separate effects of the individual active compounds. This is not merely a supplementary or additive effect, but rather a genuine synergistic effect which was not to be foreseen.

The synergistic combinations of active compounds according to the present invention are markedly superior to known active compounds conventionally used for arthropod control in agriculture crops. Furthermore, component (A) does not synergize comparably with all insecticides, e.g. (B) and/or (C) do not synergize comparably with other pyrethroids; thus there is a special coaction. The instant synergistic combinations of active compound therefore represent a valuable contribution to the art of arthropod control agents.

The compositions can be applied to a variety of insects and arthropods, both of the biting and sucking type.

From the order of the Acarina, for example, *Acarus siro*, Argas spp., Ornithodoros spp., *Dermanyssas gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scale (*Aspidiotus hederae*) and soft scale (*Lecanium hesperidum*) as well as the grape mealybug (*Pseudococcus maritimus*); thrips (Thysanoptera), such as *Hercinothrips femoralis,* and bugs, for example the beet bug (*Piesma quadrata*), the red cotton bug (*Dysdercus intermedius*), the bed bug (*Cimex lectularius*), the assassin bug (*Rhodnius prolixus*) and Chagas' (*Triatoma infestans*) and, further, cicadas, such as *Euscelis bilobatus* and *Nephotettix bipunctatus.*

In the case of the biting insects, above all there should be mentioned butterfly caterpillars (Lepidoptera) such as the diamond-back moth (*Plutella maculipennis*), the gypsy moth (*Lymantria dispar*), the brown tail moth (*Euproctis chrysorrhoea*) and tent caterpillar (*Malacosoma neustria*); further, the cabbage moth (*Mamestra brassicae*) and the cutworm (*Agrotis segetum*), the large butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella* and greater wax moth (*Galleria mellonella*), and cotton bollworm (*Heliothis zea*), and the tobacco budworm (*Heliothis virescens*).

Also to be classed with the biting insects are beetles (Coleoptera), for example the granary weevil (*Sitophilus* granarius=*Calandra granaria*), the Colorado beetle (*Leptinotarsa decemlineata*), the kock beetle (*Gastrophysa viridula*), the mustard beetle (*Phaedon cockleariae*), the blossom beetle (*Meligethes aeneus*), the boll weevil (*Authonomus grandis*), the raspberry beetle (*Buturus tometosus*), the bean weevil (Bruchidius-=*Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamai*), the drugstore beetle (*Stegobium paniceum*), the yellow mealworm (*Tenebrio molitor*) and the saw-toothed grain beetle (*Oryzae-philus surinamensis*), and also species living in the soil, for example wireworms (Agriotes spec.) and larvae of the cockchafer (*Melolontha melolontha*), cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as an ants, for example the garden and (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further gnats for example mosquitoes such as the yellow fever mosquito (*Aedes aegypti*), the northern house mosquito (Culexpinpiens) and the malaria mosquito (*Anopheles stephensi*).

The active compounds according to the instant invention can be utilized, if desired, in the form of the usual formulations on compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, suspensions, emulsifiable, concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressure, such as methylene chloride; inert dispersible liquid diluent carriers, including inert organic solvents, such as aromatic hydrocarbons (e.g. benzene, toluene, xylene, alkyl napthalenes, etc.), halogenated, especially chlorinated, aromatic hydrocarbons (e.g. chlorobenzenes, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselguhr, etc.), and ground synthetic minerals (e.g., highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with such solid and/or liquid dispersible carrier vehicle and/or with other known compatible active agents, especially plant protection agents, such as other insecticides or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compounds are present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g., a surface active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compounds or by applying a liquid composition containing the same, via very effective atomizing equipment, in finely divided form, e.g., average particle diameter of from 50–100 microns, or even less, i.e., mist form, for example by airplane crop spraying techniques. Only up to at most about a few liters/hectare are needed, and often amounts only up to about 0.5 to 1 pound per acre are sufficient. In this process it is possible to use highly concentrated liquid compositions with said liquid carrier vehicles containing from about 20 to about 95% by weight of the active compounds or even the 100% active substances alone, e.g. about 20–100% by weight of the ective compounds.

Furthermore, the present invention contemplates methods of selectively killing, combating or controlling pests, which comprises applying to at least one of correspondingly (a) such pests and (b) the corresponding habitat thereof, i.e., the locus to be protected, e.g., to a growing crop, to an area where a crop is to be grown or to a domestic animal, a correspondingly combative or toxic amount, i.e., a pesticidally effective amount, of the particular active compounds of the invention alone or together with a carrier vehicle as noted above. The instant formulations or compositions are applied in the usual manner, for instance by spraying, atomizing vaporizing, scattering, dusting, watering, squirting, sprinkling, pouring, fumigating, and the like.

It will be realized, of course, that the concentration of the particular active compounds utilized in admixture with the carrier vehicle will depend upon the intended application. Therefore, in special cases it is possible to go above or below the aforementioned concentration ranges.

The unexpected superiority and outstanding activity of the particular compositions of the present invention are illustrated, without limitation, by the examples hereinbelow.

The tests were generally run as follows:

Lepidoptera

Routine evaluations are made on 4-day old lepidoptera larvae including *Heliothis virescens*, *Heliothis zea*, *Spodoptera frugiperda*, and *Trichoplusia ni*. Compounds are sprayed on cotton seedlings alone at effective rates and lower, and in all possible combination sequences on cotton leaves. Treated leaves are placed in one ounce plastic cups and one larvae is added to each cup with ten cups per treatment for each species. This trial is conducted twice and evaluations are made after two days on the number of dead larvae.

Mites

Mites are evaluated by infesting bean plants two days prior to treatment and then dipping infested leaves in test solutions with three plants per treatment. Evaluations are made on the number of live mites after seven days and separate counts are made on nymphs and adults.

Ovicide

Heliothis eggs are used to test ovicidal activity. Adults lay eggs on cotton plants which are then sprayed after holding for one or two days. Evaluations are made on number of eggs hatched and on larval activity and mortality.

The spray solutions were prepared by using the commercial formulations of:

Compound A (BAYTHROID 2E, an emulsifiable concentrate containing 240 grams of active ingredient per liter),
Compound B (BOLSTAR 6E an emulsifiable concentrate containing 6 pounds of active ingredient per gallon),
Compound C (in example No. 2 FUNDAL 95 SP, a soluble powder containing 95% active ingredient, in all other examples GALECRON 4E, an emulsifiable concentrate containing 480 grams active ingredient per liter),
Compound D (PEROPAL 50 WP, a wettable powder containing 50% active ingredient),
Compound E (PLICTRAN 50 WP, a wettable powder containing 50% active ingredient),
Compound F (VENDEX L, a emulsifiable concentrate containing 42% active ingredient).

Stock solutions in water were made of each chemical. For the individual treatments, the proper amount of the respective stock solution was filled up with water to contain the indicated concentration in percent, or the weighed amount of chemical, which would give the indicated rate in 1000 liters per hectare, the gallonage used in the trials. For the combinations, the respective amounts of stock solutions were poured together and then filled up with water to their final strength as explained above.

The data are compiled in tabular form as shown hereinbelow. Assessments are made on the range of efficacy, and the interactions between compounds based on these data.

In the tables, the symbols have the following meanings:

∴ moderate synergy
◯ pronounced synergy

EXAMPLE 1

| | Spodoptera frugipoda, % kill of larvae | | | | |
|---|---|---|---|---|---|
| | | Compound C | | | |
| Wt. % | 0 | .0008 | .004 | .02 | .1 |
| 0 | 0 | 10 | 0 | 0 | 10 |
| Comp. A .00016 | 10 | 20 | 15 | 30 | 20 |
| .0008 | 15 | ∴40∴ | ∴40∴ | ∴45∴ | ◯60◯ |
| .004 | 60 | ◯100◯ | ∴80∴ | ◯95◯ | ∴85∴ |
| .02 | 100 | 100 | 100 | 100 | 100 |

EXAMPLE 2

| | Trichoplusia ni. % kill of larvae | | | | |
|---|---|---|---|---|---|
| | | Compound C | | | |
| Wt. % | 0 | .0008 | .004 | .02 | .1 |
| 0 | 0 | 40 | 5 | 30 | 25 |
| Comp. A .00016 | 55 | 90 | 85 | 100 | 80 |
| .0008 | 95 | 95 | 100 | 100 | 100 |
| .004 | 100 | 100 | 100 | 100 | 100 |
| .02 | 100 | 100 | 100 | 100 | 100 |

It is noted that the 40% kill for 0.0008% of B is apparently an anomalous result, based on the other values and experience from other trials.

EXAMPLE 3

The results in the tables are averages of two trials.

(a) H. virescens, 2 day old eggs, % kill

| | Grams active ingredient per Hectare | Compound C | | | | | |
|---|---|---|---|---|---|---|---|
| | | 0 | 12.5 | 25 | 50 | 100 | 200 | 400 |
| | 0 | 0 | 33 | 33 | 14 | 73 | 72 | 90 |
| Comp. A | 1.25 | 2 | ◯76◯ | ◯90◯ | ◯85◯ | 88 | — | — |
| | 2.5 | 21 | ◯85◯ | ◯90◯ | ◯91◯ | 96 | 97 | — |
| | 5.0 | 66 | 92 | 98 | ◯100◯ | 97 | 95 | — |
| | 10 | 95 | 98 | 100 | 100 | 100 | 100 | — |
| | 20 | 97 | 100 | 100 | 100 | 100 | 100 | — |
| | 40 | 100 | — | — | — | — | — | — |

-continued

| (b) Grams active ingredient per hectare Permethrin | Compound C | | | | | |
|---|---|---|---|---|---|---|
| | 0 | 50 | 100 | 200 | 400 | 800 |
| 0 | 0 | 13 | 42 | 79 | 92 | 77 |
| 5 | 0 | 25 | 49 | 60 | 23 | — |
| 10 | 0 | 4 | 55 | 69 | 70 | — |
| 20 | 30 | 70 | 54 | 71 | 58 | — |
| 40 | 33 | 83 | 72 | 79 | 79 | — |
| 80 | 90 | 82 | 87 | 77 | 70 | — |
| 160 | 98 | 100 | 79 | 97 | 89 | — |

Whereas the results from table 3a shown synergy between A and C, the table from 3b wherein a different synthetic pyrethroid (Permethrin) was substituted for A shows that there is less positive interaction and in some instances even antagonism, e.g. where Permethrin is added to 400 g of C.

EXAMPLE 4

| | | Tetranychus urticae, % kill after 7 days | | | | |
|---|---|---|---|---|---|---|
| | | | Compound C | | | |
| | Wt. % | 0 | .0008 | .004 | .02 | .1 |
| | 0 | 0 | 0 | 10 | 50 | 70 |
| Comp. A | .00016 | 0 | 0 | 0 | 30 | 70 |
| | .0008 | 0 | 0 | 50 | 50 | 80 |
| | .004 | 0 | 0 | 70 | 70 | (95) |
| | .02 | 0 | 10 | 70 | (98) | (100) |

EXAMPLE 5

| | Active Ingredient in grams/ hectare | Compound B | | |
|---|---|---|---|---|
| | | 0 | 40 | 200 |
| (a) Tetranychus urticae, % kill after 7 days | | | | |
| Comp. A | 0 | 0 | 0 | 0 |
| | 8 | 0 | 0 | 0 |
| | 40 | 0 | 0 | 0 |
| | 200 | 0 | 0 | (80) |
| Comp. A | 0 | 0 | 0 | 50 |
| | 8 | 20 | 0 | 70 |
| | 40 | 0 | (70) | (95) |
| | 200 | (100) | 98 | 100 |
| (c) All treatments received Compound C at 200 gr a.i/H | | | | |
| Comp. A | 0 | 30 | (98) | (100) |
| | 8 | 50 | 100 | 98 |
| | 40 | (70) | 98 | 100 |
| | 200 | (80) | 100 | 100 |

The table from (b) shows that certain combinations of A+B+C synergize even relative to A+B and C, such doubly synergistic values being shown in double circles.

(c) shows that a high amount of C synergizes both A and B.

EXAMPLE 6

| | Tetranychus urticae, % kill after 7 days | | | | |
|---|---|---|---|---|---|
| | Active ingredient in gram/ hectare | Compound D | | | |
| | | 0 | 1.6 | 8 | 40 | 200 |
| Comp. A | 0 | 0 | 0 | 80 | 100 | 100 |
| | 1.6 | 0 | 0 | 95 | 98 | 100 |
| | 8 | 0 | 60 | 98 | 100 | 100 |
| | 40 | 0 | 70 | 98 | 100 | 100 |
| | 200 | 0 | 90 | 100 | 100 | 100 |

EXAMPLE 7

| | Tetranychus urticae, % kill after 7 days | | | | |
|---|---|---|---|---|---|
| | | Compound E | | | |
| | Wt. % | 0 | 0.0008 | 0.004 | 0.02 | 0.1 |
| Comp. A | 0 | 0 | 80 | 80 | 100 | 100 |
| | 0.00016 | 0 | 70 | 80 | 100 | 100 |
| | 0.0008 | 0 | 100 | 95 | 100 | 100 |
| | 0.004 | 0 | 100 | 98 | 100 | 100 |
| | 0.02 | 0 | 100 | 100 | 100 | 100 |

EXAMPLE 8

| | Tetranychus urticae, % kill after 7 days | | | | |
|---|---|---|---|---|---|
| | Active ingredient in gram/ hectare | Compound F | | | |
| | | 0 | 8 | 40 | 200 | 1000 |
| Comp. A | 0 | 0 | 0 | 0 | 0 | 50 |
| | 1.6 | 0 | 0 | 0 | 0 | 80 |
| | 8 | 0 | 50 | 40 | 40 | 95 |
| | 40 | 0 | 20 | 70 | 100 | 100 |
| | 200 | 0 | 80 | 95 | 95 | 70 |

It will be understood that the specification and examples are illustrative but not limitative of the present invention and that other embodiments within the spirit and scope of the invention will suggest themselves to those skilled in the art.

What is claimed is:

1. A synergistic arthropodicidal composition comprising an arthropodicidally effective amount of (A) cyano-(4-fluoro-3-phenoxyphenyl)-methyl 3-(2,2-dichlorovinyl)-2,2-dimethyl-cyclopropanecarboxylate plus (C) $N^1$-(4-chloro-O-tolyl)-N,N-dimethyl-formamidine, in weight ratio of A:C of about 1:0.2–125.

2. A composition according to claim 1, wherein the weight ratio is about 1:1–10.

3. A composition according to claim 1 wherein the weight ratio of A:C is 1:0.2.

4. A composition according to claim 1 wherein the weight ratio of A:C is 1:1.

5. A composition according to claim 1 wherein the weight ratio of A:C is 1:5.

6. A composition according to claim 1 wherein the weight ratio of A:C is 1:125.

7. A synergistic arthropodicidal composition consisting essentially of an arthropodicidally effective amount of (A) cyano-(4fluoro-3-phenoxyphenyl)-methyl 3-(2,2-dichlorovinyl)-2,2-dimethyl-cyclopropanecarboxylate plus (C) $N^1$-(4-chloro-O-tolyl)-N,N-dimethyl-formamidine, in weight ratio of A:C of about 1:0.2–125.

8. A method for combating arthropods which comprises applying to such arthropods or an arthropod habitat an arthropodicidally effective amount of a composition according to claim 1.

9. A method according to claim 8, wherein the composition is applied to spider mites or to a spider mite habitat.

10. A method for combating spodoptera which comprises applying to such spodoptera or to a habitat thereof a toxic amount of a composition according to claim 3.

11. A method for combating spodoptera which comprises applying to such spodoptera or to a habitat thereof a toxic amount of a composition according to claim 4.

12. A method for combating spodoptera which comprises applying to such spodoptera or to a habitat thereof a toxic amount of a composition according to claim 5.

13. A method for combating spodoptera which comprises applying to such spodoptera or to a habitat thereof a toxic amount of a composition according to claim 6.

* * * * *